United States Patent [19]

Angyan et al.

[11] Patent Number: 4,943,678
[45] Date of Patent: Jul. 24, 1990

[54] PESTICIDAL COMPOSITION

[75] Inventors: Sandor Angyan, Budaors; Gyula Oros; Istvan Racz, both of Budapest; Tamas Detre, Nagymaros, all of Hungary

[73] Assignee: Chinoin Gyogyszer es Vegyeszeti Termekek Gyara Rt, Budapest, Hungary

[21] Appl. No.: 748,740

[22] Filed: Jun. 25, 1985

[30] Foreign Application Priority Data

Jun. 25, 1984 [HU] Hungary ............................... 2454/84

[51] Int. Cl.$^5$ ...................... A01N 43/82; A01N 43/76
[52] U.S. Cl. ...................................... 514/374; 514/362
[58] Field of Search ................. 514/362, 374; 548/230

[56] References Cited

U.S. PATENT DOCUMENTS

| | | | |
|---|---|---|---|
| 2,742,462 | 4/1956 | Gever | 548/230 |
| 2,759,931 | 8/1956 | Drake et al. | 548/230 |
| 3,154,543 | 10/1964 | Ebetino et al. | 548/230 |

OTHER PUBLICATIONS

Merck Index, 10th Ed. (1983), p. 613, #4175.
Merck Index, 10th Ed. (1983), p. 148, #1042.

Primary Examiner—Joseph A. Lipovsky
Attorney, Agent, or Firm—Herbert Dubno; Jonathan Myers

[57] ABSTRACT

The invention relates to pesticidal composition against bacterial plant diseases comprising as active ingredient a nitrofurane derivative of the general Formula I

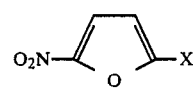

/I/ wherein X represents a group of the Formula a/

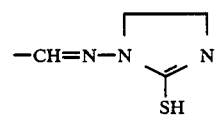

/a/ or /b/ -

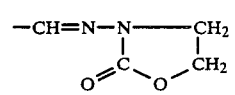

/b/ and optionally one or more known fungicidal active ingredient/s/ in a total amount of 1–99% by weight, whereby the ratio of the active ingredient of the general Formula I to the known fungicidal active ingredient/s/ amounts to 1:99–99:1, preferably 1:9–9:1 if the composition comprises two active ingredients and 1:9:0.5–1:1:5, preferably 1:4:1–1:1:4 if the composition comprises three active ingredients, respectively, in admixture with suitable inert solid or liquid carrier/s/ or diluent/s/ and usual auxiliary agents such as wetting agents, dispersing agents, adhesives, antifoaming agents and/or antifreezers.

6 Claims, 1 Drawing Sheet

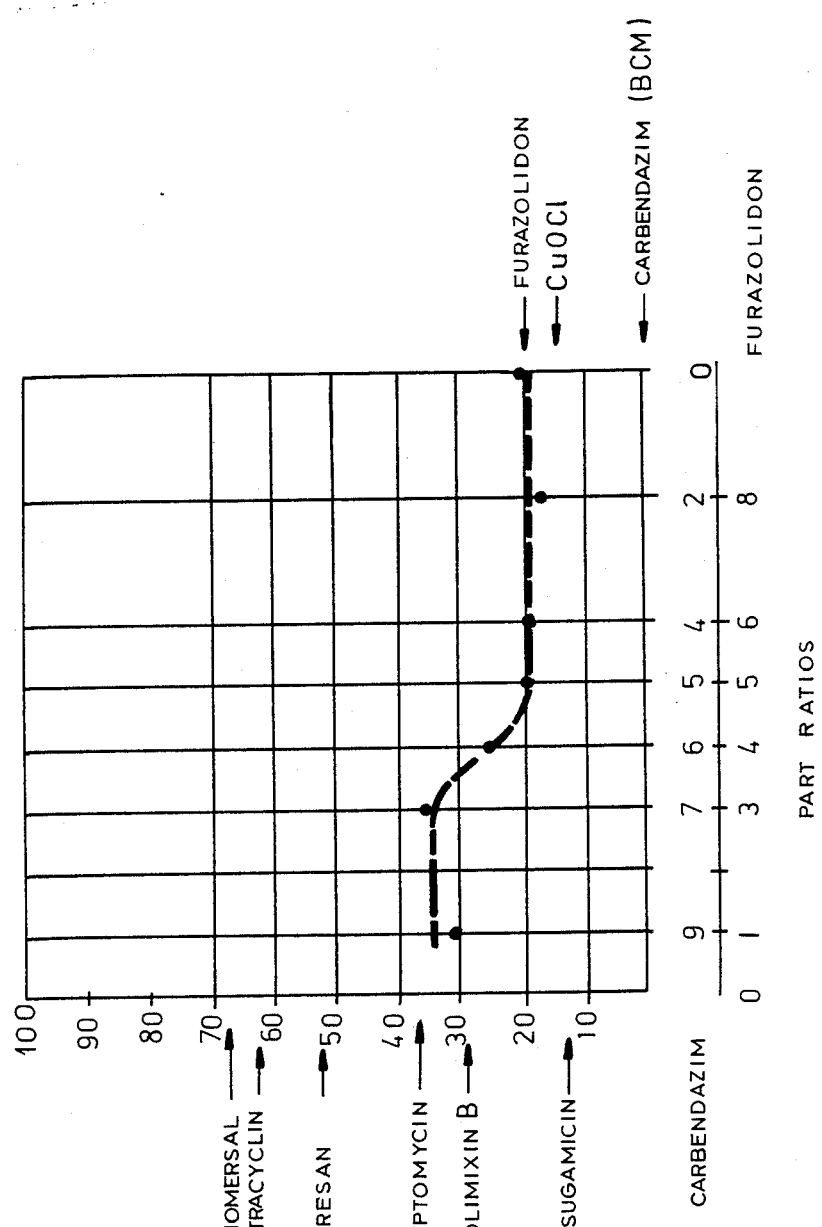

PESTICIDAL COMPOSITION

FIELD AND GENERAL DESCRIPTION OF THE INVENTION

This invention relates to pesticidal compositions against bacterial plant diseases, a process for the preparation thereof and a method for the use of the same in agriculture for the control of bacterial plant diseases.

According to an aspect of the present invention there are provided pesticidal compositions against bacterial plant diseases comprising as active ingredient a nitrofurane derivative of the Formula I

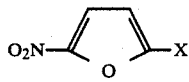

wherein X represents a group of the Formula a

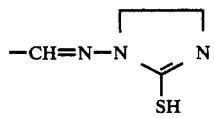

or /b/ -

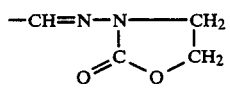

and optionally one or more known fungicidal active ingredients in a total amount of 1–99% by weight, whereby the ratio of the active ingredient of the Formula I to the known fungicidal active ingredients amounts to 1:99 to 99:1, preferably 1:9 to 9:1 if the composition comprises two active ingredients and 1:9:0.5 to 1:1:5, preferably 1:4:1 to 1:1:4 if the compositions comprises three active ingredients, in suitable inert solid or liquid carriers or diluents and usual auxiliary agents such as wetting agents, dispersing agents, adhesive, antifoaming agents and/or antifreezers.

The compositions of the present invention are useful in the control of the following bacterial diseases or bacterial and fungal diseases of plants, respectively:

*Agrobacterium tumefaciens* O
*Agrobacterium tumefaciens* C-58
*Agrobacterium tumefaciens* B-6
*Agrobacterium radiobacter* K-84
*Erwinia uredowora*
*Erwinia carotovora var, atroseptica*
*Erwinia carotovora*
*Corynebacterium michiganense*
*Corynebacterium nebraskense*
*Xanthomona spp.*

Fusarium spp., Rhizoctonia spp., Botrytis spp., Sclerotinia spp., Alternaria spp., Penicillium spp., Aspergillus spp., Rhizopus spp.

The pesticidal compositions may contain in addition to the compound of the Formula I one or more known fungicidal active ingredients. For this purpose any suitable known contact or systemic fungicide may be used. The aim of the use of the further fungicide is to broaden the activity spectrum of the composition. Thus preferably the following fungicidal active ingredients may be applied:

1-butylcarbamoyl-benzimidazole-2-methyl-carbamate (Benomyl):
2-methoxycarbonylamino-benzimidazole (MBC);
1,2-bis-3-methoxycarbonyl-thioureido/-benzene (Thiophanate-methyl);
2-(4-thiazolyl)-benzimidazole (Thiabendazol);
zinc-ethylene-bis-dithiocarbamate (Zineb);
manganese-ethylene-bis-dithiocarbamate (Maneb);
manganese zinc-ethylene-bis-dithiocarbamate (Mancozeb);
tetramethyl-thiuram-disulfide (TMTD);
N-trichloro-methylthio-tetrahydro-phthalimide (Captan).

The compositions of the present invention are particularly suitable for the protection of propagating materials—e.g. seeds, tubers, bulbs, cuttings, before sowing or during storage.

BACKGROUND OF THE INVENTION

In addition to the large number of infecting fungal diseases plants are also subject to damages caused by various phytopatogenic bacteria.

The most important characteristics of the diseases induced by plant patogenic bacteria are summarized by Klement [Plant Protection (1982) No. 3].

| Symptom group | Pest | Bacterial material responsible for the symptoms |
|---|---|---|
| Necrosis stain-diseases | Pseudmonas | Bacterial polysaccharides. Materials inducing necrosis |
| Cancerous growth, wilting withering | Xanthomonas | Chlorogenic toxins, Necrogenic toxins |
| | Corynebacterium | Cellulose decomposing enzymes; toxins causing withering |
| Soft rot | Erwinia | Pectin decomposing enzymes |
| Tumors | Agrobacterium | Information material coded by plasmids |

From the group of phytopatogenic bacteria the species which infect the propagating materials—seeds, tubers, bulbs, tree-nursery propagating materials—are particularly significant. Thus *Corynebacterium michiganense* on tomato and *Corynebacterium nebraskaense* on maize can be mentioned. Agrobacterium tumefactiens induces large tumors on the propagating materials of various fruit-species and vine and makes the infected material unsuitable for use. From the phytopatogenic bacteria Erwinia species causing soft rot on stored crops having a high liquid and juice content and that of propagating materials (tubers, bulbs, onion-roots) are particularly harmful because of the significant economic damage caused.

*Erwinia carotovora var. atroseptica* is responsible for the soft rot of potato during storage and in the absence of effective protection the damages caused may be particularly significant.

According to Pintér [Plant Protection "Növényvédelem" (1982) No. 3] in the case of a soft rot of 5% the damage appearing on potato may be estimated to a sum higher than 100 million forints.

In prior art the significance of the simultaneous appearance of bacterial (*Erwinia carotovora var. atroseptica*) and fungal diseases is discussed in detail [see e.g. Stachewich: 1974., Nachr. Blatt Pflschutz., 28. (2)., Wellving: Sweed. Seed. Assoc. (31); Anonym: Merkbl. des Pflschutz, 1974, (10)].

Thus potato may be simultaneously attacked by fungal and bacterial diseases both during storage and after sowing.

Pesticidal active ingredients used against simultaneously occuring fungal and bacterial diseases are summarized in Table 1, where the prior art citations are disclosed as well.

TABLE 1

| Pest | Active ingredient | Citation |
|---|---|---|
| Erwinia carotovora var. atroseptica | phenyl-alanine, ammonialiase, polyphenol streptomycin, kanalicin, neomycin, erithromycin, chloramphenicol | Gupta, Tripathi Indian J.E. 1976. 4. [3.] Albergiana, Phytopath. Zeit. 81. [2.] |
| Fusarium | Benomyl | Leach, 1975 USDA 17. Jellis, Taylor Ann. Appl. Biol. |
| | thiabendazol | Munzel, Bayer Land. 1976. 52. [2.] |
| Erwinia carotovora var. atr. + Fusarium | MBC + chloramphenicol, benomyl + chloramphenicol, Zineb + + chloramphenicol Zineb + chloramphenicol | Ratba, Spez. Pflsch. 1977. 1. Burth, Jahn Akad. Landw. Wiss. [140] Anonymus, Gops. Soil. 1975. 30. [1.] |
| Erwinia + Pseudomonas | antibiotic + fungicide | Sahurai, 1975. J. Antibiotics, 29. [11.] |

However, none of the above compositions is suitable for complete protection and therefore antibiotics are used for the control of bacterial infection. In most of the countries however, the use of antibiotics in agriculture is prohibited.

OBJECT OF THE INVENTION

It is the object of the present invention to overcome the deficiencies of known methods in the control of bacterial plant diseases. More particularly the object of the present invention is to elaborate
an efficient protection against bacterial plant diseases and
a plant protecting agent being suitable for the simultaneous control of bacterial and fungal diseases.

SPECIFIC DESCRIPTION

It is known from veterinary practice that nitrofurane derivatives are active against certain gram-negative bacterium strains. However, the prior art is completely silent in teaching any use of nitrofurane derivatives in plant protection.

According to pre-tests and in vitro tests carried out in connection with the present invention the following nitrofurane test-compounds are used:

H-819, Furazolidone=5-nitro-furfurylidene-3-amino-2-oxazolidone;

CH-1237, Nitrofurantoine: N-(5-nitro-furfurylidene-2)-1-amino-hydantoine;

CH-1552=3-(5-nitro-furfuryldene-amino)-imidazole-2-thiol;

CH-2007=2-(5-nitro-furfurylidene-amino)-4-chloromethyl-5-(2-chloroethyl)-thiazole;

CH-2011=2-(5-nitro-furfurylidene-amino)-4-methyl-5-(2-chloroethyl)-thiazole;

CH-2103=2-(5-nitro-furfurylidene-amino)-4-methyl-5-(2-hydroxyethyl)-thiazole.

The results are summarized in Table 2.

TABLE 2

| | Antibacterial effect of nitrofurane derivatives on axenial cultures | | | | | |
|---|---|---|---|---|---|---|
| | MIC mg/ml | minimal inhibitory concentration | | | | |
| Bacterium strain | 819 | 1237 | 1552 | 2011 | 2013 | |
| Agrobacterium tumefaciens 0 | 4–8 | 1000 | 8–16 | A | A | |
| Agrobacterium tumef. C-58 | 4–8 | 1000 | 8–16 | A | A | |
| Agrobacterium tumef. B 6 | 4–8 | 1000 | 8–16 | A | A | |
| Agrobacterium rad.bac. K-84 | 2–4 | 1000 | 4–8 | A | A | |
| Erwinia herbicola D 5 | 1000 | A | 1000 | A | A | |
| Erwinia Uredovora | 0.2–05 | A | 2–4 | A | A | |
| Erwinia atroseptica | 4–8 | A | 8–10 | A | A | |
| Erwinia carotovora | 4–8 | A | 8–10 | A | A | |
| Pseudomonas lachrymans | 8–16 | A | 30–60 | A | A | |
| Pseudomonas mors-prunorum | 1000 | A | 1000 | A | A | |
| Pseudomonas phaseolicola | 30–60 | A | 60–120 | A | A | |
| Pseudomonas pisi | 250–500 | A | 1000 | A | A | |
| Pseudomonas fluorescens | 1000 | A | 1000 | A | A | |
| Rhizobium japonicum | 8–16 | A | 30–60 | A | A | |
| Xanthomonas alfalfae | 30–60 | A | 60–120 | A | A | |
| Xanthomonas campestries | 1000 | A | 1000 | A | A | |
| Xanthomonas fus.pv.phaseoli | 30–60 | A | 60–120 | A | A | |
| Xanthomonas pelragonii | 30–60 | A | 60–120 | A | A | |
| Xanthomonas vesicatoria | 1000 | A | 1000 | A | A | |
| Xanthomonas orisae | | | | | | |
| Corynebacterium fascians | 15–30 | A | 60–120 | A | A | |

TABLE 2-continued

Antibacterial effect of nitrofurane derivatives on axenial cultures

| Bacterium strain | MIC mg/ml 819 | minimal inhibitory concentration | | | |
|---|---|---|---|---|---|
| | | 1237 | 1552 | 2011 | 2013 |
| Corynebacterium flaccumfac. | 30–60 | A | 60–120 | A | A |
| Corynebacterium michiganense | 4–8 | A | 8–16 | A | A |
| Corynebacterium nebraskense | 4–8 | A | 8–16 | A | A |
| Corynebacterium oortii | 60–120 | A | 250–500 | A | A |

A = >1000 mg/ml

It is noteworthy that *Erwinia carotovora* and *Agrobacterium tumefaciens* strains are highly sensitive towards compound No. 819 but moderately sensitive towards compound No. 1552.

On the basis of the pre-tests further in vitro tests are carried out in order to determine the biological activity of certain nitrofurane derivatives and combinations of nitrofurane derivatives with fungicidal active ingredients.

SPECIFIC EXAMPLES

Further details of the present invention are to be found in the following Examples without limiting the scope of protection to the said Examples.

TABLE 3

Effect of carbendazin on the bactericidal activity of Furazolidon against certain bacterium strains

| Species | Host plant | 9K + 1F | 4K + 1F | 7K + 3F | 3K + 2F | 1K + 1F |
|---|---|---|---|---|---|---|
| Agrobacterium tumefaciens | sugar beet | 10 | 10 | no | no | no |
| Corynebacterium betae | sugar beet | 10 | no | no | no | no |
| Erwinia carotovora | potato | 10 | no | no | no | no |
| Erwinia atroseptica | potato | 100 | 10 | 10 | no | no |
| Xanthomonas campestris | cabbage | 100 | 100 | 100 | 10 | no |
| Xanthomonas pelragonii | oelargonium | 10 | 10 | 10 | 10 | no |
| Xanthomonas vesicatoria | tomato | 100 | 10 | 10 | 10 | no |
| Xanthomonas fuscans | bean | 10 | no | no | no | no |
| Xanthomonas malvacearum | cotton | 10 | 10 | 10 | no | no |
| Xanthomonas carotae | carrot | 10 | no | no | no | no |
| Xanthomonas stewartii | maize | 10 | 10 | 10 | no | no |
| Xanthomonas oryzae | rice | 100 | 100 | 10 | no | no |

Carbendazim per se does not inhibit the growth of any of the above species even in a dose of 9000 mg/l. The word "no" indicates that the effect of furazolidone is the same as that of the control plate comprising no carbendazine.

EXAMPLE 1

Activity data of the test compounds against *Erwinia carotovora var. atroseptica* in Petri-dish test The test is carried out with five replicates for each dose by using a nutrient medium suitable for the isolation of *Erwinia carotovora*.

The bacterium is propagated in a nutrient medium on slant agar and with the bacterium suspension isolated from a pure culture the nutrient medium cooled to 40°–50° C. is inoculated by the following method.

Into Petri-dishes having a diameter of 10 cm a nutrient medium (20 ml) is poured and after solidification 4 holes are bored into each Petri-dish. Into each hole 0.1 ml of the suspension is applied. Incubation is carried out at 25° C. The results are disclosed in Table 4.

TABLE 4

| Treatment | | | Point of time of evaluation (in hours after treatment) | | | |
|---|---|---|---|---|---|---|
| Test Substance | Concentration mg/ml | Dose ml | 24 | 48 | 72 | 96 |
| | | | Inhibition zone (mm) | | | |
| CH-819 | 1.5 | 0.1 | 0 | 1–2 | 5 | 10 |
| | 1.5 | 0.1 | 0 | 2 | 10 | 15 |
| CH-1237 | 1.0 | 0.1 | 0 | 0 | 0 | 0 |
| | 1.5 | 0.1 | 0 | 0 | 0 | 0 |

TABLE 4-continued

| Treatment | | | Point of time of evaluation (in hours after treatment) | | | |
|---|---|---|---|---|---|---|
| Test Substance | Concentration mg/ml | Dose ml | 24 | 48 | 72 | 96 |
| | | | Inhibition zone (mm) | | | |
| CH-1552 | 1.0 | 0.1 | 0 | 0 | 1 | 3–5 |
| | 1.5 | 0.1 | 0 | 1 | 1–2 | 5–7 |
| CH-2007 | 1.0 | 0.1 | 0 | 0 | 0 | 0 |
| | 1.5 | 0.1 | 0 | 0 | 0 | 0 |
| CH-2011 | 1.0 | 0.1 | 0 | 0 | 0 | 0 |
| | 1.5 | 0.1 | 0 | 0 | 0 | 0 |
| CH-2013 | 1.0 | 0.1 | 0 | 0 | 0 | 0 |
| | 1.5 | 0.1 | 0 | 0 | 0 | 0 |
| CH-819 + Benomyl | 1.5 + 1.5 | 0.2 | 0 | 1–2 | 5–6 | 8–10 |
| CH-819 + MBC | 1.5 + 1.5 | 0.2 | 0 | 1 | 5 | 8–10 |
| CH-1552 + MBC | 1.5 + 1.5 | 0.2 | 0 | 0 | 1–2 | 3–5 |
| Benomyl | 1.5 | 0.1 | 0 | 0 | 0 | 0 |
| MBC | 1.5 | 0.1 | 0 | 0 | 0 | 0 |

It appears from the above data that on the basis of the size of the inhibition zone nitrofurane derivatives Nos. CH-819 and CH-1552 proved to be active against *Erwinia carotovora var. atroseptica* in a concentration of 1.0–1.5 mg/ml at a dose of 0.1 ml/hole. Benomyl and MBC do not increase the bactericidal activity.

EXAMPLE 2

Potato tubers (Desire species) are cut into two pieces; holes (depth 15 mm, diameter 10 mm) are bored at an approximately same distance from each other (twice 5 holes).

0.1 ml of an aqueous suspension comprising *Erwinia carotovora var. atroseptica* bacterium is added dropwise into the holes (0.1 ml into each hole). The test compound is poured into the holes pre-treated with the bacterium with the aid of a micropipette after half an hour. The treated and infected tubers are kept in a humid chamber for three days (72 hours) whereupon the evaluation is carried out. The holes are cut in two parts perpendicular to the original cutting plane, the soft rot pieces are stratched out and weighed. The efficiency of the treatment is evaluated by comparing with the untreated control on the basis of the following scale:

Infection category

0 = 0–5%
1 = 6–10%
2 = 11–25%
3 = 25–50%
4 = above 50%.

The above percental values represent the weight of the stratched material pectolized by *E. carotovora* stroseptica related to the weight of the control.

"0" indicates the most favorable and "4" indicates the least effective treatment.

The results are summarized in Table 5.

TABLE 5

| Treatment | | | | | | | |
|---|---|---|---|---|---|---|---|
| | Ratio | Dose (mg/ml) | | | | | |
| Test compound | (% by weight) | 50 | 25 | 12 | 6 | 3 | 1.5 |
| CH-819 | 100 | 0 | 0 | 0 | 0 | 0 | 1 |
| CH-1237 | 100 | 4 | 4 | 4 | 4 | 4 | 4 |
| CH-1552 | 100 | 0 | 0 | 0 | 1 | 2 | 2 |
| CH-2007 | 100 | 3 | 4 | 4 | 4 | 4 | 4 |
| CH-2011 | 100 | 3 | 3 | 4 | 4 | 4 | 4 |
| CH-2012 | 100 | 3 | 4 | 4 | 4 | 4 | 4 |
| CH-2013 | 100 | 2 | 3 | 4 | 4 | 4 | 4 |
| Benomyl | 100 | 3 | 3 | 4 | 4 | 4 | 4 |
| MBC | 100 | 3 | 4 | 4 | 4 | 4 | 4 |
| CH 819 + Benomyl | 50 + 50 | 0 | 0 | 0 | 0 | 0 | 0 |
| CH-819 + MBC | 50 + 50 | 0 | 0 | 0 | 0 | 1 | 2 |
| CH-819 + MBC + Dithane M-45 | 50 + 25 + 25 | 0 | 0 | 0 | 0 | 1 | 2 |
| CH-1552 + MBC | 50 + 50 | 0 | 0 | 0 | 0 | 2 | 3 |

Similarly to the Petri-dish test it has been found that in the above test nitrofurane derivatives Nos. CH-819 and CH-1552 and combinations thereof with fungicides are effective.

Out of the combinations of fungicides and bactericides the combination of CH-819+MBC+Dithane M-45 (active ingredient Mancozeb) in a ratio of 50%+25%+25% proved to be the most active.

The present invention is based on the recognition that compounds Nos. CH-819 and CH-1552 exhibit strong effect against phytopatogenic bacteria belonging to the *Erwinia genus*. The pesticidal compositions of the present invention are highly suitable for the control of bacterial diseases or bacterial and fungal diseases, respectively.

The plant protecting agents may be formulated in various forms and the composition is selected by taking into consideration the conditions of application, the plant cultivating technology and the available machinery.

In order to protect tubers, bulbs, root-stocks and rhizomes during storage it is necessary to subject the said propagating materials to treatment before storage. The said technology is substantially identical with or similar to the so-called "dressing process" generally used for the pre-sowing treatment of the above parts of the plants and seedlings. The said dressing methods can be carried out at different points of time.

The pesticidal compositions of the present invention may be formulated in usual and conventional forms e.g. powders, water dispersible powders, suspension concentrates, granules etc.

The preparation of the compositions of the present invention comprises two fundamental steps which may be often combined with each other:

The first step comprises the preparation of an active ingredient having a suitable particle. It has been found that in order to achieve the desired result 70% of the particles must have a particle size below 10 μm. This may be carried out by two methods. According to the said methods the active ingredient is ground to the desired particle size by a dry process (e.g. in an air current mill) or a wet method (e.g. in a pearl or sand mill). According to a preferred form of realization of the process the chemical reaction used for the preparation of the active ingredient is carried out in such a manner that an active ingredient having the desired particle size should be obtained; thus the use of the expensive grinding apparatus having a high energy demand can be rendered superfluous.

The second step is the preparation of the desired formulation whereby the particles of the active ingredient are contacted with the auxiliary agents, carriers, diluents, adhesives, activity increasing compounds, coloring agents etc.

Water dispersible powders

It is an essential requirement that the particles of the active ingredient should be readily dispersible in water and that the suspension, when applied onto the parts of the plant to be protected, should provide a uniform coating. For this reason the mixture comprises so-called wetting agents. The chemical structure of the said compounds comprises an apolar and polar moiety. From the chemical point of view the said compounds belong to the following groups:

Anion active compounds

Carboxylates
  Soaps
  Amino carboxylic acids having high molecular weight and their salts
  Acylated and condensed amino carboxylic acids
Sulfates
  Sulfates of fatty acids
  Sulfates of fatty acid derivatives
  Alkyl sulfates
Sulfonates
  Sulfonates of fatty acids, fatty acid esters, fatty acid amides etc.
  Sulfonates of fatty alcohols, ethers, nitriles
  Alkyl sulfonates
  Sulfonates of esters, ethers or amides
  Sulfonates of aromatic or hydroaromatic compounds
  Aralkyl sulfonates of high molecular weight
  Aromatic sulfonic acid esters, ethers or amides.
Phosphorous compounds
  Phosphates, amidophosphates
  Phosphites
  Phosphonates
  Phosphinates
Borates of high molecular weight
Fluorine compounds
Non-ionic compounds
  Polyhydroxides
  Alkylene oxides of high molecular weight
  Substituted polyglycol ethers
  Ethoxylated alkyl amides Substituted polyglycol esters
Polyglycol sulfates
Cation active compounds
  Amine derivatives
  Onium compounds
  Amine oxides
Amphoteric compounds
  Protein derivatives
  Substituted and sulfobetain
Substituted amino carboxylic acids, amino sulfuric acids and amino phosphoric acids
  Cyclic compounds
Polymers
  Anion active compounds
  Non-ionic compounds
  Cation active compounds
  Amphoteric compounds When selecting the said auxiliary agents reference is made e.g. to the following book: Kurt Lindner, Tenside, Textilhilfsmittel, Waschrohstoffe, Wissenschaftliche Verlaggesellschaft MbH, Stuttgart.

It is a further important requirement that on use the suspension formed from the wetted and dispersed particles of the active ingredient should be stable i.e. during storage no sedimentation should take place which may cause undesired change of concentration. This may be achieved by using suitable dispersing agents. The said compounds are giant molecules acting as protecting colloides. For this purpose e.g. calcium, sodium or ammonium salts of lignin sulfonates, water-soluble polymers, mucus etc. may be used.

As carriers or filling materials preferably ground minerals (e.g. China-clay, kaolin, bentonite, calcium carbonates, gypsum etc.) may be applied.

The wettable powder compositions may also contain adhesives. The said compounds may be particularly preferably water soluble giant organic polymers. Preferred representatives of the said compounds are enumerated below: carboxymethylated starch, carboxymethylated cellulose, polyvinyl pyrrolidone.

In order to increase the effect the compositions of the present invention may contain inorganic salts (e.g. sodium sulfate), organic acids (e.g. tartaric acid), vegetable and mineral oils etc.

In order to improve storage properties the compositions may also comprise synthetic high surface silicic acids, aluminium oxides etc.

For the user foaming may constitute serious problems and this may be overcome with the aid of antifoam agents. For this purpose emulsions of oils may be used. The said antifoam agents may be prepared by admixing the suitable emulsifier system-selected by taking into consideration the oil to be emulsified with the oil, pouring the mixture thus obtained into water and stirring with a suitable stirrer. If water is an undesired component of the formulation, the oil comprising the emulsifier may be incorporated into the composition. In this case the oil exhibits its effect when the active ingredient is brought into a suspension. It is important that the antifoam agent used should possess self-emulsifying properties. As antifoam agents emulsions of vegetable or mineral oils—particularly emulsions of silicone oils—may be used too.

Antifoam emulsions may also be obtained by partially saponifying vegetable or mineral oil with sodium or potassium hydroxide. The advantage of the stable emulsions thus obtained is that the materials used are of a natural origin and are readily and completely decomposed during the biological life procedures of the plants.

Suspension concentrates play a rapidly increasing role in plant procection technology. Said compositions comprise the active ingredient in the form of a suspension and the auxiliary agents in the form of an aqueous and/or oily solution. The water and/oil acts as solvent and as filling agent (diluent) as well. The suspension concentrates show the following advantages:

since the said compositions are suspensions, the risks of inevitable dust-formation are eliminated;
on suspending powder compositions the slow wetting caused by the weak wettable properties of the active ingredient particles often constitutes serious problems; in the case of suspension concentrates this drawback does not occur;
auxiliary agents improving adhesion and other properties are kept in solution and therefore clotting is avoided and accordingly on spraying the nozzles are not obstructed and uniform spraying is achieved;
the compositions show good floating properties.

Suspension concentrates may generally comprise wetting and dispersing agents enumerated in connection with the wettable powders. The said suspension concentrates may also contain agents increasing the stability of the suspension, namely giant water-soluble organic molecules. For this purpose e.g. carbohydrate derivatives, synthetic polymers, agents improving the structure of the suspension (e.g. artificial synthetic silicic acids, aluminium oxides and bentonite of large surface, organophilic bentonite etc.) may be used.

Freezing point decreasing (antifreezing) agents may be important components of aqueous suspensions. For this purpose preferably polyols—particularly ethylene glycol—may be applied.

The stability of the suspension may be affected in a preferred manner by using emulsions of oils of vegetable, animal or mineral origin at a suitable ratio. The said additive improves the biological activity of the composition too.

Soil dwelling microorganisms may be controlled by the so-called soil desinfecting method. This may preferably be carried out by using granulated pesticides. The said composition is incorporated into the soil. Under the effect of the moisture the active ingredient is set free, migrates in the soil and ensures an environment suitable for the undisturbed and proper growth of the cultivated plants by destroying the undesired pests.

Pesticidal granules may be prepared by admixing the active ingredient ground to a suitable particle size, the carriers, fillers and auxiliary agents (e.g. wetting agents, dispersing agents, adhesives, agents regulating the delivery of the active ingredient, disintegrating agents etc.) with water, kneading the mixture, pressing the mass thus obtained through a sieve having a suitable mash-size or granulating by an other known method, drying and grinding or subjecting to spray-drying. According to another method the particles of the active ingredient are applied onto the surface of a suitable carrier previously brought to the desired particle size distribution (e.g. organic or inorganic granules). If one or all the active ingredients are liquids a carrier granule having a suitable porosity is used and the liquid is absorbed in the said porous granule. In the case of active ingredients being partly solids and partly liquid one may proceed by dispersing the solid active ingredient in the liquid one and absorbing the liquid thus obtained in a porous carrier whereby the solid particles are adhered to the carrier. When soluble active ingredients are used one may proceed preferably by preparing a solution from the active ingredients, absorbing the solution thus obtained in the carrier and evaporating the solvent.

As adhesives preferably substances occuring in nature (e.g. cellulose derivatives, sugars, gelatine, gums, oils of vegetable, animal or mineral origin, fats etc.) may be used. One may also use synthetic adhesives e.g. polyvinyl alcohol, polyvinyl acetate, polyacrylic acid, polyacrylic amide, polyvinyl pyrrolidone etc.

On the basis of the in vitro tests we have carried out in vivo tests to determine the bactericidal and fungicidal effect. The compositions used in said tests are prepared according to the following examples.

EXAMPLE 3

An active ingredient having the following particle size distribution is prepared:

| | |
|---|---|
| above 10 /μm | 20.3% |
| 5–10 /μm | 31.0% |
| below 5 /μm | 48.7% |

The measurements are carried out on an ultrasonic micro sieve set (manufacturer Retsch).

100 kg of the active ingredient (CH-819), 3 kg of Diotilan, 5 kg of Totanin B, 4 kg of Neuburg chalk and 1 kg of Tylose C are weighed in a 600 l Loedige-type rapid stirrer through a grinding granulator. The mixture is stirred for 10 minutes and in order to ensure intimate contact of the components it is ground in an Alpine UP 315 mill with a performance of 200 kg/hour. Final distribution is provided by homogenizing the mixture in a 300 l Nautamix and the product is then packed.

The floating capacity of the CH-819 80 WP thus obtained amounts to 89% (measured in a 0.5% suspension according to the WHO standards).

EXAMPLE 4

By using a CH-819 active ingredient having the particle size distribution according to Example 3 the following composition is prepared:

| | |
|---|---|
| CH-819 | 160 kg |
| Evidet 27 | 2 kg |
| Alkylene | 6 kg |
| Boresperse NA | 10 kg |
| Tylose C 1000 p | 1 kg |
| Aerosil 300 | 1 kg |
| Calcium carbonate pp | 20 kg |

The wettable powder formulation thus obtained is particularly suitable for bactericidal treatment of potato and root plants due to the high active ingredient content of the formulation.

EXAMPLE 5

An effective control of simultaneous fungal and bacterial infections can be achieved by adding a systemic fungicide to the composition in addition to the bactericide. Thus the following composition is prepared:

| | | |
|---|---|---|
| Benomyl | 60 kg | |
| CH-819 | 40 kg | (paricle size distribution as in Example 3) |
| Genapol PGM | 10 kg | |
| Sulfite waste powder | 10 kg | |
| Calciumcarbonate pp | 80 kg | |

The components are introduced into a 600 l Loedige rapid stirrer through a grinding granulator except the Genapol PGM which is a viscous wetting agent having a water content of 50%. The mixture is stirred for 3 minutes whereupon the Genapol is directly added (i.e. not through the grinding granulator) and homogenized for 10 minutes. The mixture is dried in a KFSZ-250-SH type fluidization drier equipped with a stirrer. The mixture is then ground in an Alpine AS-200 air current mill, subjected to post-homogenization in a 300 l Nautamix stirrer and packed.

EXAMPLE 6

The following composition is prepared:

| | | |
|---|---|---|
| CH-819 | 26.4 kg | (particle size distribution as in Example 3) |
| Benomyl | 68.0 kg | |
| Mankozeb | 20.0 kg | |
| Diotilan | 2.0 kg | |
| Evidet 27 | 2.0 kg | |
| Tylose H 20 | 2.0 kg | |
| Aerosil 300 | 1.0 kg | |
| Rodamin B | 0.6 kg | |
| Calciumcarbonate pp | 68.0 kg | |

The mixture is ground in an Alpine AS-200 air current mill to an average particle size of 5 μm, thereafter thoroughly homogenized in a 300 l Nautamix stirrer with 10.0 kg of dimethyl sulfoxide and packed.

EXAMPLE 7

183.35 g of water are admixed with 55 g of ethylene glycol. In the mixture thus obtained 16.5 g of Tensiofix B 4725 and 16.5 g of Tensiofix CG 11 are dissolved at 40° C. In the solution thus obtained 143 g of CH-819 having a particle size distribution according to Example 3 are dispersed with the aid of a stirrer having a high shear force (Ultra-Turrax).

A mixture of 99 g of paraffin oil and 11 g of Triton X-45 is added to the suspension under further dispersing stirring. The stirring is continued until a homogenous oil-solid-water system is obtained. To the system a 2% by weight aqueous solution of 27.5 g of Tensiofix 821 is added under stirring. The mixture is stirred until a homogeneous mixture is formed. On stirring foaming takes place and for this reason at the end of this step 1.1 g of Tensiofix L 051 antifoaming agent are added. The composition thus obtained is well adhered onto the parts of the plants, the suspension possesses an excellent stability and the floating capacity is above 95%.

EXAMPLE 8

228.3 kg of water are admixed with 7 kg of ethylene glycol with the aid of a dissolver. In the solution thus obtained the following components are dissolved under further stirring:
1.5 kg of Atlox 4875
0.5 kg of Atlox 1225
1.5 kg of Atlox 4852/b.

In the solution of the above surfactants 21 kg of CH-819 and 34 kg of Mancozeb active ingredients are suspended with the aid of a dissolver.

The suspension is ground in a 50 l pearl mill with a performance of 200 l/hour to an average solid particle size below 5 μm. The suspension is introduced into an apparatus equipped with a stirrer and 9 kg of paraffins oil and 1 kg of Triton X 45 are added under stirring. After complete admixture a 2% aqueous solution of 5 kg of Tensiofix 821 is added under further stirring. The mixture is stirred whereupon the suspension emulsion system thus obtained is stabilized by passing through a desaggregator. At the end of this step and before final formulation 0.3 kg of Tensiofix L 051 antifoam agent is added. The combined pesticidal formulation thus obtained possesses excellent spraying properties. The composition is better and more readily adhered to the parts of the plants than the hitherto used pesticides.

EXAMPLE 9

The following composition is prepared:

| | |
|---|---|
| 20 parts by weight of | MBC |
| 20 parts by weight of | CH-819 |
| 3 parts by weight of | Tensiofix B 4725 |
| 3 parts by weight of | Tensiofix CG 21 |
| 10 parts by weight of | Ethylene glycol |
| 5 parts by weight of | a 2% aqueous solution of Tensiofix 821 |
| 40 parts by weight of | Water |

EXAMPLE 10

Effect of CH-819 on infecting pests during thee storage of potato (bacteria and fungi)

Potato tubers (Somogy Gyöngye species) are treated before storing. 25 kg of tubers are used in each replicate and the number of replicates amounts to 5. The tubers are stored in a potato store-room until the evaluation took place.

The number of ill tubers and that of tubers infected by the given disease are counted (No.).

The results are summarized in Table 6.

TABLE 6

| | Composition | | | | | |
|---|---|---|---|---|---|---|
| Characteristics feature | Ex. 3 2 kg/to | Ex. 5 3 kg/to | Ex. 6 3 kg/to | Ex. 7 2 l/to | Ex. 8 2 l/to | Control |
| No. of ill tubers | 27.4 | 22.8 | 19.7 | 31.0 | 25.4 | 53.0 |
| Fusarium dry rot | 18.0 | 12.5 | 12.5 | 21.0 | 15.0 | 29.0 |
| Alternaria dry rot | 6.0 | 5.8 | 2.4 | 5.6 | 5.2 | 8.0 |
| *Erwinia c. v. atr.* | 3.4 | 4.5 | 5.8 | 4.4 | 5.2 | 16.0 |

Compositions comprising only a nitrofurane derivative as active ingredient are effective only against Erwinia. However, rot caused by Fusarium and Alternaria can be controlled by using a composition which contains a fungicide in addition to the nitrofurane derivative. Combinations according to Examples 5, 6 and 9 exhibit the best effect in controlling infection and particularly composition according to Example 6(13+34+10% by weight combination of CH-819+Benomyl+Mankoceb)gives the best results.

EXAMPLE 11

After digging up potato tubers of a propagation degree of UT-1 (Desire species) are treated on the 23rd October with certain doses of the test compounds in the form of wet dressing (15 l of treating liquid/to). The potato collected with a machine is purified before treatment, sorted, the lumps, residual stems and ill tubers are removed. 200 tubers are used for each treatment and 3 replicates are carried out for each dose. The treated tubers are put into cloth sacks and placed into aerated large pile storage equipments. During storage the temperature is adjusted below 15° C. and the relative moisture content amounts to 80-90%. The changing environmental parameters of the prismatic storing equipment (temperature, moisture content) provide suitable conditions for the pathogenic pests.

Evaluations are carried out on the 31st April of the next year. The weight and ratio of the healthy and infected tubers, the rate of abating and the infection degree of the pests is determined. The results are summarized in Table 7.

TABLE 7

| | | Weight of tuber | | | | |
|---|---|---|---|---|---|---|
| Test compound Example | Dose kg/to | Added amount (kg) | Final weight (kg) | Fusarium infection % | Bacterial rot, tubers % | Alternaria dry rot |
| 3. + Agrocit (50% Benomyl) | 1.5 + 1.8 | 200 | 180.4 | 23.8 | 7.8 | 12.6 |
| 2. + Kolfugo 25 FW (MBC)* | 1.0 + 1.0 | 200 | 189.5 | 20.4 | 5.4 | 7.9 |
| 5. | 3.0 | 200 | 185.6 | 23.4 | 8.5 | 12.5 |
| 6. | 2.0 | 200 | 178.4 | 18.7 | 6.3 | 3.2 |
| 9. | 2.0 | 200 | 175.2 | 21.7 | 5.8 | 8.9 |
| Control | — | 200 | 107.4 | 63.3 | 38.6 | 13.2 |

*Disclosed in DD-PS 209950

The results of the above industrial scale test prove the effectiveness of the combination of the present invention against plant diseases. On untreated control Fusarium dry rot cause the largest losses but the damages induced by Erwinia car. var. atrospetica are high as well. Against Fusarium-Erwinia particularly the composition according to Examples 5 and 9 while against Fusarium+Erwinia+Alternaria the composition according to Example 6 gave the most effective results.

EXAMPLE 12

Potato (Desire species) is treated before planting with certain doses of the test compounds by using a dressing machine type GUMOTOX at a dose of 6.5 l of treating liquid/to. Planting is carried out with the aid of a 4-Sa BP-75 planting machine. The size of the plots is 0.5 ha, the number of replicates amounts to 3 and the weight of seed tubers is 2.8 to/ha.

15 days after sowing the plants not sprouted as a result of Rhizoctonia germ infection are counted, on an area of 4×50 running meters the Thizoctonia shoot-infection is determined (200 shoots each) the infection of the tubers is counted by inspecting 200 tubers each and the ratio of the tubers having a seed size of 4-6 cm is determined. The results are summarized in Table 8.

TABLE 8

| Treatment | Dose kg, l/to | Germ. 4 × 50 No. of sprouted plants | Inf. No. of killed germs pro | Rhizoct. infected sprouts F | Rhizoct. infected sprouts % | Tubers No/stem | Crops q/ha | Ratio of seeding K % |
|---|---|---|---|---|---|---|---|---|
| Agrocit | 3.0 | 387 | 3 | 0.71 | 47.5 | 8.8 | 41.0 | 125.6 |
| Ex. 3. + Agrocit | 1.0 + 2.0 | 397 | 0 | 0.71 | 56.5 | 9.5 | 45.6 | 131.0 |
| Ex. 9 | 2.5 | 394 | 1 | 0.68 | 44.3 | 9.2 | 45.0 | 129.1 |
| Ex. 6 | 3.0 | 396 | 0 | 0.62 | 39.7 | 9.6 | 47.8 | 138.4 |
| Untreated | — | 375 | 25 | 1.6 | 83.0 | 7.1 | 37.2 | 100 |

As a result of dressing carried out before sowing the crops yield and the weight of potato crops (%) increased to a significant extent.

EXAMPLE 13

Sensitivity of plant pathogens and bacteria towards mixtures of carbendazime and furazolidone of various ratio In vitro bactericidal tests are carried out. The minimal inhibitory concentration of various mixtures of the said two xenobiotics is determined as follows:

Various ratio mixtures of the two antibiotics are formulated and amixed with the nutrient medium having the composition disclosed below. The final concentration of furazolidone amounts to 1000, 100, 10, 1 and 0.1 mg/l, respectively. The concentration of carbendazime in the medium varies depending on the mixing ratio.

The relative efficiency related to furazolidone is calculated on each tested species for each mixing ratio (25 species). The results are calculated by using the formula of McKiney (Sváb 1981: Biometrical methods in research, Mezögazdasági Kiadó Budapest).

The results are graphically plotted in the sole FIGURE of the drawing.

It has been found in a surprising manner that if carbendazime dominates in the mixture the bactericidal activity of furazolidine is significantly increased, namely in certain cases by 100 times (see Table 3). This synergism may be observed particularly in the Xanthomonas genus.

Nutrient medium

Agar powder nutrient medium (Human OEV) 26 g; Bacto agar 2.5 g; glucose 3 g; yeast extract 1 g; Bacto peptone 2g; potassium dihydrogen phosphate 0.55 g; potassium chloride 0.1 g; sodium chloride 0.1 g; magnesium sulfate 0.125 g; calcium chloride 0.125 g; iron citrate 0.02 g; micro element solution according to Hoagland and Arnon 1 ml (related to 1 liter of the nutrient medium). The pH value of the nutrient medium is adjusted to 6.5 by adding a 2N ammonium hydroxide solution.

Inoculation

The test compounds are added to the nutrient medium having a temperature of 50° C. before plate moulding. Inoculation is carried out after solidification according to usual methods of bacteriology.

EXAMPLE 14

Elimination of *Xanthomonas oryze* infection in rice by seed-dressing

The pathogen is isolated from seeds originating from the Far-East and showing unidentified infectedness. These seeds are used in the treatment. 250 seeds are treated in each treatment before germination with mixtures of Kolfugo 25 FW and Furazolidine 30 FW used in suitable dose (Example 7). Since Kolfugo 25 FW was completely inactive against pure cultures it was not used for the treatment of seeds. The seeds are subjected to pre-germination in wet filter paper for 48 hours (this is a model of the so-called "dopog" method) whereupon 200 seeds having a germ-fundament are selected for each treatment. These seeds are punctured with a needle at the stem of the radicle. The thus treated seeds are sown in a sterile soil and grown in a phytotrone (12 hours' illumination, at 28° C. during the day and at 25° C. during the night) for 14 days whereupon the results are evaluated.

| No. of sown seeds | Fura- zolidone g/t | BCM g/t | No. of sprouted seeds | No. of ill seeds | Ratio of ill seeds % |
|---|---|---|---|---|---|
| 200 | 0 | 0 | 178 | 61 | 34.2 |
| 200 | 300 | 0 | 184 | 5 | 2.7 |
| 200 | 300 | 700 | 178 | 0 | 0 |
| 200 | 150 | 1350 | 170 | 0 | 0 |

What we claim is:

1. A method of combating phytopathogenic bacteria selected from the group consisting of Agrobacteria, Erwinia, Xanthomonas, Pseudomonas, and Corynebacterium, which comprises the step of applying onto a plant, the soil, or the environment thereof, an antibacterial composition, comprising a phytopathogenic bactericidally effective amount of the compound of the Formula (I)

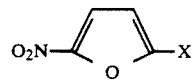

wherein X is the group of the Formula (a)

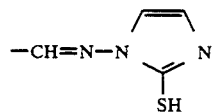

or the Formula (b)

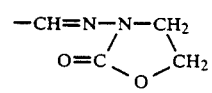

in combination with an agriculturally acceptable inert carrier.

2. The method of combating phytopathogenic bacteria defined in claim 1 wherein the antibacterial composition further comprises a fungicide selected from the group consisting of:
1-butyl-carbamoyl-benzimidazole-2-methyl-carbamate;
2-methoxycarbonylamino-benzimidazole;
1,2-bis-(3-methoxycarbonyl-thioureido)-benzene;
2-(4-thiazolyl)-benzimidazole;
zinc-ethylene-bis-dithiocarbamate;
manganese-ethylene-bis-dithiocarbamate;
manganese and zinc ethylene-bis-dithiocarbamate;
tetramethyl-thiuram-disulfide; and
3-trichloromethylthio-tetrahydro-phthalimide,
wherein the ratio of the antibacterial compound of the Formula (I) to the fungicide is 1:99 to 99:1.

3. The method of combatting phytopathogenic bacteria defined in claim 2 wherein the ratio of the antibacterial compound of the Formula (I) to the fungicide is 1:9 to 9:1.

4. The method of combatting phytopathogenic bacteria defined in claim 2 wherein the plant is a potato plant.

5. The method of combatting phytopathogenic bacteria defined in claim 1 wherein the plant is a potato plant.

6. The method of combatting phytopathogenic bacteria defined in claim 1 wherein the phytopathogenic bacteria belong to the Erwinia genus or the Xanthomonas genus.

* * * * *